(12) United States Patent
Khalil

(10) Patent No.: US 10,925,695 B2
(45) Date of Patent: Feb. 23, 2021

(54) CUSTOMIZED POROUS SUPRACRESTAL IMPLANT AND MATERIALS AND METHODS FORMING THEM

(71) Applicant: Wael Khalil, Beirut (LB)

(72) Inventor: Wael Khalil, Beirut (LB)

(*) Notice: Subject to any disclaimer, the term of this patent is extended or adjusted under 35 U.S.C. 154(b) by 281 days.

(21) Appl. No.: 15/789,987

(22) Filed: Oct. 21, 2017

(65) Prior Publication Data
US 2018/0110593 A1    Apr. 26, 2018

Related U.S. Application Data

(60) Provisional application No. 62/467,967, filed on Mar. 7, 2017.

(51) Int. Cl.
| | | |
|---|---|---|
| A61C 8/00 | (2006.01) | |
| A61F 2/28 | (2006.01) | |
| A61L 27/54 | (2006.01) | |
| A61B 17/80 | (2006.01) | |
| A61C 8/02 | (2006.01) | |
| A61F 2/30 | (2006.01) | |

(52) U.S. Cl.
CPC .......... *A61C 8/0013* (2013.01); *A61C 8/0016* (2013.01); *A61C 8/0031* (2013.01); *A61C 8/0068* (2013.01); *A61C 8/0095* (2013.01); *A61F 2/2803* (2013.01); *A61L 27/54* (2013.01); *A61B 17/8071* (2013.01); *A61C 8/0006* (2013.01); *A61C 8/0009* (2013.01); *A61C 2008/0046* (2013.01); *A61F 2002/30011* (2013.01); *A61F 2002/30014* (2013.01); *A61F 2002/3092* (2013.01); *A61L 2430/12* (2013.01)

(58) Field of Classification Search
CPC . A61B 17/8071; A61C 8/0006; A61C 8/0009; A61C 8/0013; A61C 8/0016; A61C 8/0031; A61C 8/0068; A61C 8/0095; A61C 2008/0046; A61F 2/2803; A61F 2002/30011; A61F 2002/30014; A61F 2002/3092; A61L 27/54; A61L 2430/12
USPC .................................................. 433/172–176
See application file for complete search history.

(56) References Cited

U.S. PATENT DOCUMENTS

| | | | |
|---|---|---|---|
| 10,010,609 B2* | 7/2018 | D'Agostino | ....... A61B 17/7097 |
| 10,525,168 B2* | 1/2020 | D'Agostino | ........... A61K 47/34 |
| 10,525,169 B2* | 1/2020 | D'Agostino | .......... A61F 2/2846 |

(Continued)

*Primary Examiner* — Matthew M Nelson
(74) *Attorney, Agent, or Firm* — Ellenoff Grossman & Schole LLP; James M. Smedley; Alex Korona

(57) ABSTRACT

The present invention generally relates to osseointegrated implants. In particular, embodiments of the present invention relate to extraosseous implants, for example, supra crestal implants, that are configured to substantially continuously cover the 3D topography of a top and a lateral surface of a bone, for example, a crestal and a lateral surface of the jaw. For example, the implants may be used on partially or completely edentulous jaws. Also, embodiments of the present invention relate to such implants made from biocompatible material of suitable porosity and elastic modulus. Specifically, embodiments of the present invention relate to improved implants suitable for implantation to bone deficient in quantity or quality, such as severely resorbed jaw bone. Further embodiments relate to a unique composite material comprising PEEK, bioglass and PMMA, and formed using triacrylate.

3 Claims, 3 Drawing Sheets

(56) References Cited

U.S. PATENT DOCUMENTS

| | | | | |
|---|---|---|---|---|
| 2007/0015110 A1* | 1/2007 | Zhang | .................. | A61C 8/0012 |
| | | | | 433/173 |
| 2016/0106838 A1* | 4/2016 | D'Agostino | ........... | A61K 47/02 |
| | | | | 623/23.51 |
| 2016/0346435 A1* | 12/2016 | D'Agostino | .............. | A61F 2/28 |
| 2017/0239396 A1* | 8/2017 | D'Agostino | .......... | A61L 27/446 |
| 2019/0117848 A9* | 4/2019 | D'Agostino | ............ | A61L 27/46 |
| 2019/0314557 A9* | 10/2019 | D'Agostino | ............ | A61L 27/46 |

* cited by examiner

CUSTOMIZED POROUS SUPRACRESTAL IMPLANT AND MATERIALS AND METHODS FORMING THEM

CROSS-REFERENCE TO RELATED APPLICATIONS

This application includes a claim of priority under 35 U.S.C. § 119(e) to U.S. provisional patent application No. 62/467,967, titled "Customized porous supracrestal implant", and filed Mar. 7, 2017; and also claims foreign priority to GB 1618533.2, titled "Composite implant material", and filed Nov. 3, 2016; GB 1617889.9, titled "Artificial bone composite", and filed Oct. 21, 2016; GB 1702688.1, titled "Composite implant material", and filed Feb. 20, 2017; and GB 1702686.5, titled "Artificial bone composite", and filed Feb. 20, 2017; each of which is incorporated herein by reference in its entirety.

FIELD OF THE INVENTION

The present invention generally relates to osseointegrated implants. In particular, embodiments of the present invention relate to extraosseous implants, for example, supra crestal implants, that are configured to substantially continuously cover the 3D topography of a top and a lateral surface of a bone, for example, a crestal and a lateral surface of the jaw. For example, the implants may be used on partially or completely edentulous jaws. Also, embodiments of the present invention relate to such implants made from a bioactive biocompatible material of suitable porosity and elastic modulus. Specifically, embodiments of the present invention relate to improved implants suitable for implantation to bone deficient in quantity or quality, such as severely resorbed jaw bone.

BACKGROUND

The successful outcome of implantation may depends on many factors and may include the implant materials used and their biocompatibility, the macroscopic and microscopic surface structure, the quantity and quality of the bone that accepts the implant, surgical technique, absence of micromotions during healing after implantation, loading conditions (equilibrated forces applied to the implant). One or more of these factors, and additional ones, can lead to an unsuccessful outcome, and the implant may not heal properly, or may lack stability even after healing.

Osseointegrated implants are widely used as hard tissue endosseous replacements in artificial bones, joints, and dental implants. Osseointegration is a direct structural and functional connection between ordered, living bone and the surface of a load carrying implant, it is critical for implant stability, and is considered a prerequisite for implant loading. The processes of osseointegration involves an initial interlocking between bone and implant, and later, biological fixation through continuous bone ingrowth.

Various different materials have been used for osseointegrated implants, for example commercially pure titanium (cp), Titanium-6 Aluminum-4 Vanadium (TI-6AL-4 V) alloy. While generally biocompatible, implants made of these materials may exhibit in rare cases unwanted reactions such as soft tissue reactions, e.g. inflammatory reactions due to ion release of the metals. As a hard tissue replacement, the high elastic modulus of titanium and its alloys (55-114 GPa) is generally viewed as a biomechanical advantage, in particular in load bearing areas.

Certain polymers have been used as osseointegrated implants to avoid some of the problems associated with metal implants. These include PEEK (Polyether ether ketone), which has acceptable biocompatibility and mechanical and chemical resistance properties, but a Young's modulus (elastic modulus) of 3.6 GPa, which is lower than that of bone.

Other implant materials that have been used include ceramic and zirconium.

Known implant types/configurations include endosseous implants, plate implants, transosteal implants, and subperiosteal implants.

Endosseous implants (i.e. within the bone, e.g. screws within the jaw bone) require sufficient bone quantity and quality for implantation, and in case of bone deficiency or atrophy require successful bone regeneration or reconstruction before implantation. Plate implants are usually made of pure titanium grade one, their implantation requires extensive invasive surgery by a specialized practitioner, and the osseointegration of the plate to the host bone can be unsuccessful because it relies usually only on primary or mechanical stability.

Implants that have been used for deficient or atrophied bone include transosteal implants (also known as lateral basal or disc implants), and subperiosteal implants.

Transosteal (i.e. through the bone) implants pass through the jawbone laterally, require extensive surgery by a trained practitioner, and successful implantation requires sufficient quantity and quality/stability of remaining cortical bone.

Subperiosteal (i.e. on top of the bone) implants are conventionally made of surgical vitallium (chrome, cobalt, molybdenum), and titanium is also used. A subperiosteal implant consist of a metal framework or lattice that attaches on top of the jawbone but underneath the periosteum and gum tissue. The permucosal posts or abutments are cast to the substructures thus eliminating the need for a second stage surgery after initial healing. Subperiosteal implants rely primarily on their mechanical stability and their disadvantages include fibrous tissue proliferation and the related manufacture/casting requirements to provide a perfect fit to the jaw, and lower success rates compared to the endosseous implant, thus this type of implant is rarely used today.

Thus, implants of known structure and materials currently do not provide easy implantation, biocompatibility, and a high success rate in all clinical situations, particularly in situations where quality, quantity or stability of bone is lacking, e.g. atrophic and resorbed jaws or other bone deficiencies.

Osseointegration may be defined as a direct structural and functional connection between ordered, living bone and the surface of a load-carrying implant. Osteointegration is considered to be important for implant stability, and for implant loading The implant-tissue interface is a dynamic region of interaction. The interaction involves biomaterial and biocompatibility issues, but also alteration of a mechanical environment. Osseointegration involves an initial interlocking between alveolar bone and the implant body, and later, biological fixation through continuous bone apposition and remodeling toward the implant.

Commercially pure titanium (cp) is widely used as an implant material as it is highly biocompatible, it has good resistance to corrosion, and no toxicity on macrophages or fibroblasts, lack of inflammatory response in peri-implant tissues and it is composed of an oxide layer and has the ability to repair itself by reoxidation when damaged.

Another material used for implants, Titanium-6 Aluminum-4 Vanadium (TI-6AL-4 V) alloy exhibits soft tissue reactions very similar to those reported to cp Ti, Titanium and titanium alloys are widely used as hard tissue replacements in artificial bones, joints, and dental implants.

Using polymer instead of metal can be safer and is a known possibility. PEEK (Polyether ether ketone) is one alternative to titanium for osseointegrated implant. The bone to implant contact (BIC) and osseointegration of titanium is superior to that of PEEK. It would be desirable to provide a bone implant material that is polymer based and has improved BIC and osseointegration.

There remains an ongoing need for improved bone implant materials that are biocompatible, promote healing, capable of load bearing, able to be manufactured efficiently and shaped as desired. Thus, it is desired to provide a bone implant material that allows at least some of the aforementioned objectives to be achieved.

Further, composites comprising PMMA formed by mixing with the monomer acrylate are less known and used in implants and lack various desirable characteristics relating e.g. to porosity and typically have a modulus that does not match that of natural bone very well, in addition to poor bioactivity.

Therefore, there is a need in the art for osseointegrated implants with high biocompatibility and stability that promote healing, can be shaped flexibly (to adapt to the patient's particular anatomy) and manufactured easily and where other implants such as endosseous or transosseous implants cannot be used, or have a low success rate. In particular, there is a need for an implant design and/or material that can be used in case of bone deficiencies such as atrophic and/or resorbed jaws, especially where severe bone resorption has been occurred. Also there is a need for implants that do not require invasive reconstructive surgery. Still further there is a need for implant designs that are compatible with different materials, including metals, polymers and composites. Further there is a need for supracrestal implants to the jaw bone that are biocompatible and stable when used on healthy and on deteriorated bone. These and other features and advantages of the present invention will be explained and will become apparent to one skilled in the art through the summary of the invention that follows. Further there is a need for new and improved implant materials.

SUMMARY OF THE INVENTION

The present invention generally relates to osseointegrated implants. In particular, embodiments of the present invention relate to extraosseous implants, for example, supracrestal implants, that are configured to substantially continuously cover the 3D topography of a top and a lateral surface of a bone, for example, a crestal and a lateral surface of the jaw. For example, the implants may be used on partially or completely edentulous jaws. Also, embodiments of the present invention relate to such implants made from a bioactive biocompatible material of suitable porosity and elastic modulus. Specifically, embodiments of the present invention relate to improved implants suitable for implantation to bone deficient in quantity or quality, such as severely resorbed jaw bone.

In an embodiment, provided is an extraosseous implant configured to substantially continuously cover the 3D topography of a top and a lateral surface of a bone, wherein the implant is made of a bioactive biocompatible osseointegratable material.

In an embodiment, provided is an extraosseous implant wherein the implant is a supracrestal dental implant, wherein the implant is configured to substantially continuously cover the 3D topography of the crestal and lateral parts of the jaw, wherein the implant comprises a plurality of abutments configured for attachment of a dental prosthesis.

In an embodiment, provided is an extraosseous implant wherein the biocompatible material has an elastic modulus from 3 to 114 GPa.

In an embodiment, provided is an extraosseous implant wherein the biocompatible bioactive material is selected from the group consisting of a composite comprising a polymer and a ceramic, wherein the polymer is selected from one or more of PEEK, PMMA and chitosan, and wherein the ceramic is selected from one or more of Bioglass, hydroxyapatite, and tricalcium phosphate.

In an embodiment, provided is an extraosseous implant wherein the biocompatible bioactive material is selected from the group consisting of a metal selected from a titanium oxide, and a titanium alloy.

In an embodiment, provided is an extraosseous implant wherein the biocompatible material has an elastic modulus from about 3 to about 30 GPa, for example from about 3 to about 7 GPa, for example about 3.6 GPa.

In an embodiment, provided is an extraosseous implant wherein the biocompatible material is a porous Titanium alloy.

In an embodiment, provided is an extraosseous implant wherein the bioactive biocompatible material is a composite polymer mixture selected from the group consisting of PEEK mixed with PMMA, PEEK mixed with Bioglass, PEEK mixed with Bioglass and PMMA, PMMA mixed with Bioglass, PMMA mixed with chitosan, and optionally one or more filler, one or more active, and one or more amphiphilic polymer promotor.

In an embodiment, provided is an extraosseous implant wherein the bioactive biocompatible material is a composite polymer mixture selected from the group consisting of PEEK mixed with PMMA, PEEK mixed with Bioglass, PEEK mixed with Bioglass and PMMA, PMMA mixed with Bioglass, PMMA mixed with chitosan, and optionally one or more filler, one or more active, and one or more amphiphilic polymer promotor.

In an embodiment, provided is an extraosseous implant wherein the bioactive is a porous composite polymer.

In an embodiment, provided is an extraosseous implant wherein the active is triacrylate to promote bone formation.

In an embodiment, provided is an extraosseous implant wherein the bioactive biocompatible material is a mixture of PMMA, PEEK and Bioglass in a ratio of about 1:1:1 (v/v/v), and the ratio of polymer to liquid triacrylate is selected from the group consisting of 0.25:1, 0.5:1, 0.75:1, 1:1, 1.25:1, 1.5:1, 1.75:1 and 2:1.

In an embodiment, provided is an extraosseous implant wherein the bioactive biocompatible material is a composite mixture of PMMA, chitosan and Bioglass in a ratio of about 1:1:1 (v/v/v).

In an embodiment, provided is an extraosseous implant wherein the bioactive biocompatible material is a composite mixture of PMMA, chitosan and Bioglass in a ratio of about 1:1:1 (v/v/v), and wherein the composite comprises an active, wherein the active is triacrylate, and the ratio of composite powder to liquid triacrylate is selected from the group consisting of 0.25:1, 0.5:1, 0.75:1, 1:1, 1.25:1, 1.5:1, 1.75:1 and 2:1 (P/TA) (v/v).

In an embodiment, provided is an extraosseous implant wherein the implant is configured for use with lateral fasteners, and the fasteners include lateral fixating screws.

In an embodiment, provided is an extraosseous implant wherein the implant is configured for use with lateral fasteners, and the fasteners include lateral fixating screws.

In an embodiment, provided is an extraosseous implant comprising an amphiphilic polymer promotor which is a block copolymer.

In an embodiment, provided is an extraosseous implant wherein the amphiphilic polymer promotor comprises aliphatic chains and anionic phosphate groups.

In an embodiment, provided is an extraosseous implant wherein the amphiphilic polymer promotor is selected from the group consisting of amphiphilic phosphorylated and non-phosphorylated 2-hydroxyethylmethacrylate.

In an embodiment, provided is an extraosseous implant wherein the implant is configured with any bioactive biocompatible material with suitable mechanical properties.

In an embodiment, provided is a composite composition comprising PEEK, bioglass and PMMA, wherein the composite is formed by mixing PEEK, bioglass and PMMA with a triacrylate liquid In an embodiment, provided is a composite composition further comprising HEMA-P.

In an embodiment, provided is a method of 3D printing a dental implant, wherein PEEK, bioglass and PMMA powders are mixed with a triacrylate liquid, and the resulting liquid mixture is used to form the implant in a 3D printing process.

DETAILED SPECIFICATION

The present invention generally relates to osseointegrated implants. In particular, embodiments of the present invention relate to extraosseous implants, for example, supra crestal implants, that are configured to substantially continuously cover the 3D topography of a top and a lateral surface of a bone, for example, a crestal and a lateral surface of the jaw. For example, the implants may be used on partially or completely edentulous jaws. Also, embodiments of the present invention relate to such implants made from a bioactive biocompatible material of suitable porosity and elastic modulus. Specifically, embodiments of the present invention relate to improved implants suitable for implantation to bone deficient in quantity or quality, such as severely resorbed jaw bone.

According to an embodiment of the present invention, the implant may be an extraosseous implant that substantially continuously covers the 3D topography of top (e.g. crestal) and a lateral surface of a the jaw, for example, a supra crestal implant, such as a supra crestal implant for a jaw bone, for attachment of a partial or full dental prothesis to a healthy jaw bone and/or or for partial or full reconstruction of a resorbed jaw bone. Extraosseous (over the crest/ridge or bone) implants, in contrast to endosseous implants, have the advantage that they better dissipate and distribute occlusal loading over a larger surface and implant/bone interface, functioning like a snow shoe on snow. One such implant may be used where otherwise several, for example 4 or more endosseous implants, would need to be used. The use of a plurality of endosseous implants is often very difficult or impossible in patients with bone deficiencies such as a severe atrophic jaw.

Figure 1:
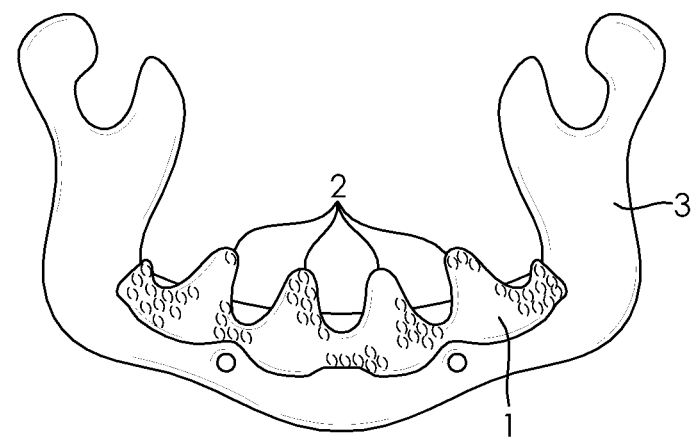
FIG. 1 shows a schematic view of an extraosseous supracrestal implant in accordance with an embodiment of the present invention.

According to an embodiment of the present invention, the implant may comprise a plurality of abutments configured from the same material in one piece, for attachment of a dental prosthesis. Generally, 2 to 8 abutments may be used, for example 4 abutments as shown in FIG. 1.

According to an embodiment of the present invention, the implant may be configured so that most of the implant mass and material are located laterally, i.e. buccal and lingual in respect of the ridge of the jaw bone), and a lesser part of the implant mass is located on top of the ridge. The part of the implant that covers the top of the ridge may mainly consist of the abutments. This has the advantage to facilitate complete closure by soft tissue after surgery and healing.

In an embodiment of the present invention, the implant may be configured so that the lateral parts of the implant (buccal and lingual) have a different composite polymer mixture, for example, they may be more porous, or less porous, or may have a higher elastic modulus, or a lower elastic modulus. Porosity and elastic modulus of the buccal and lingual side of the implant may be the same, or may be different, but preferably is the same or similar, for example the parts may have the same material and porosity.

According to an embodiment of the present invention, the implant may be configured for use with lateral fasteners, for example, holes or recesses configured for lateral fixating screws. This has the advantage of providing increased stability before healing (i.e. primary stability).

According to an embodiment of the present invention, the implant may be made of any bioactive biocompatible material of suitable elastic modulus. This material may have an elastic modulus from 3 to 114, and may be selected from polymers, composite mixtures, titanium oxide, and a titanium alloy.

Bioactive materials are materials that, unlike inert materials, are subject to bone formation and integration with the bone after implantation and during healing through direct bone apposition to the implant surface. In contrast, inert materials will not be integrated with the bone, instead, often there will be fibrous tissue deposition between the inert implant material and the bone, thus, the implant's biological or secondary stability will be weak or absent, and under load and function the implant will loosen and decrease in stability over time.

In embodiments of the present invention, the bioactive biocompatible material may be a porous metal, polymer or composite polymer mixture, and may be manufactured or configured to have elastic modulus to match that from of the bone that hosts the implant. For example, the elastic modulus may be from about 7 to about 30 GPa. This may have the advantages of protecting the bone-implant interface, increased success of implantation and improving long term implant stability.

In embodiments of the present invention, the bioactive biocompatible material may be a polymer or composite polymer mixture, and may have elastic modulus from about 3 to about 30 GPa, for example from about 3.6 GPa to about 7 GPa. This may have the advantages of protecting the bone-implant interface, increased success of implantation and improving long term implant stability.

In embodiments of the present invention, the bioactive biocompatible material may be a porous metal, porous polymer or porous composite polymer mixture, and the porosity of the implant material may be chosen or adapted during manufacture so that its elastic modulus matches that of the bone, for example, from about 3 to about 30 GPa, for example from about 3 to about 7 GPa. This may have the advantages of protecting the bone-implant interface, increased success of implantation and improving long term implant stability.

According to an embodiment of the present invention, the bioactive biocompatible material may be micro-porous or nano-porous. Illustrative examples of porous materials include porous titanium alloys.

In an embodiment of the present invention, titanium or titanium alloys may be configured with a rough surface. This may have the advantage to promote bone ingrowth, stimulate bone cells and permit better adhesion of cells and blood proteins such as fibrin.

According to an embodiment of the present invention, the bioactive biocompatible material may be a composite comprising one or more polymer and one or more ceramic material. For example, the composite may comprise a first and a second polymer, and a ceramic.

Without wishing to be bound by theory, such bioactive biocompatible polymer materials may fall within a traditional definition of a composite material. Namely, a material with at least two phases (three phases here), a continuous phase, PMMA, and PEEK and a dispersed ceramic phase (such as bioglass). The continuous phase can fill the volume and transfer loads to the dispersed phase. The dispersed phase can enhance one or more properties of the composite such as biocompatibility, promotion of bone formation and ingrowth.

In embodiments, the first polymer, the second polymer and the ceramic each may have a volume fraction of at least 10%, preferably at least 15%, preferably at least 20%, preferably at least 25%, preferably at least 30%, preferably at least 33%. The first and second polymer may be identical, in which case the volume fraction will be the combined fractions of the aforementioned, i.e. at least 20%, 30%, 40%, 50%, 60%, or 66%. Additional polymers may be used, and their combined polymer fraction may be as indicated for a single polymer, i.e. at least 20%, 30%, 40%, 50%, 60%, or 66%. In embodiments, the first polymer, the second polymer and the ceramic have substantially equivalent volumetric fractions. However, the volumetric fractions can be varied as desired depending upon the application, specifically depending upon mechanical and biological properties required by the application. For example, should reduced stiffness be required, then a fractional reduction in bioactive glass and fractional increase in biopolymer from equal volumes can be implemented.

In particular, the bioactive biocompatible composite may comprise one or more polymer selected from Poly(methyl methacrylate) (PMMA), Polyether ether ketone (PEEK), and chitosan, and a ceramic material selected from one or more Bioglass (e.g. such as 45S5, 58S, 70S30C, and S53P4), hydroxyapatite, and tricalcium phosphate. For example, the bioactive biocompatible polymer may be a polymer mixture selected from the group consisting of PMMA mixed with PEEK, and PMMA mixed with chitosan. The polymer or polymer mixture may be mixed with a ceramic, for example one or more Bioglass, a hydroxylapatite or a tricalcium phosphate, or mixtures thereof. The composite may include, for example, PEEK mixed with Bioglass, PMMA mixed with Bioglass, PEEK and PMMA mixed with Bioglass, PMMA mixed with chitosan, PEEK mixed with chitosan, and PEEK and PMMA mixed with chitosan. The composite materials may have the advantage of improved stability, in particular improved biological/secondary stability, for example improved Bone to Implant Contact (BIC), improved osseointegration, improved mechanical properties (e.g. elastic modulus), and reduced stress shielding (e.g. loss in bone density due to removal of typical stress from a bone due to the stronger material of a conventional implant). Microporous composites that comprise one or more of a resorbable material such as Bioglass or chitosan are particularly preferred for their improved bone ingrowth and resulting biological/secondary stability after healing.

In embodiments of the present invention, for example, the composite polymer mixture may comprise a polymer or polymer mixture (P) and a ceramic (C) in a substantially equivalent volumetric ratio, i.e. 2:1 P:C (v/v), or in case of two polymers 1:1:1 (P:P:C) (v/v/v). The mixtures may be varied by, for example, up to +50% or −50% volume, e.g. 2.5:0.5, (P:C), 1.5:1.5 (P:C), 1.5:0.5:1 (P:P:C), 0.5:1.5:1 (P:P:C). Alternatively, the mixtures may be varied by +40% or −40%, +30% or −30%, +20% or −20%, +10% or −10% and +5% or −5% in the ratio of polymers to ceramic. For example, the above percentages may apply to one or more of PEEK, PMMA, and chitosan, present in a higher or lower amount in the composite. Alternatively, the above percentages may apply to a ceramic present in a higher or lower amount in the composite.

In embodiments of the present invention, for example, the composite mixture may comprise PMMA, PEEK and Bioglass (e.g. 45S5) in substantially equivalent volumetric ratios, i.e. 1:1:1 (v/v). Alternatively, for example the composite mixture may comprise PMMA, chitosan and Bioglass (e.g. 45S5) in substantially equivalent volumetric ratios, i.e. 1:1:1 (v/v). Alternatively, the mixtures may be varied as described herein-above.

Bioglass is a commercially available family of bioactive glasses, composed of $SiO_2$, $Na_2O$, $CaO$ and $P_2O_5$ in specific proportions. The proportions differ from the traditional soda-lime glasses in low amount of silica (less than 60 mol %), high amount of sodium and calcium, and high calcium/phosphorus ratio. Bioglass typically refers to the FDA approved composition 45S5 (46.1 mol % $SiO_2$, 26.9 mol % CaO, 24.4 mol % $Na_2O$ and 2.5 mol % $P_2O_5$). Other compositions may include 58S (60 mol % $SiO_2$, 36 mol % CaO and 4 mol % $P_2O_5$), 70S30C: 70 mol % $SiO_2$, 30 mol % CaO, S53P4 (53 mol % $SiO_2$, 23 mol % $Na_2O$, 20 mol % CaO and 4 mol % $P_2O_5$). S53P4 is a bacterial growth inhibiting bioactive glass.

In embodiments, the ceramic or bioglass includes silicon dioxide and calcium oxide as major constituents. For example, the bioactive glass filler may comprise at least 25% by weight of each of silicon dioxide and calcium oxide.

In embodiments, the one or more polymer is a polysaccharide, specifically a positively charged polysaccharide. In embodiments, the polysaccharide is prepared from chitin. In embodiments, the polysaccharide is chitosan. Chitosan with protonated amino groups becomes a polycation that can subsequently form ionic complexes with a wide variety of natural or synthetic anionic species, such as lipids, proteins, DNA.

According to an embodiment of the present invention, the bioactive material may be a composite mixture as described herein, and may be stabilized during implantation by a bone cement, and preferably, a bioactive partially resorbable bone cement. Preferably, the bone cement may comprise one or more resorbable material, for example, one or more of chitosan and bioglass. The use of a resorbable material such as a resorbable polymer or a resorbable ceramic, or both, may have the advantage of better bone ingrowth. Suitable resorbable bone cements include, for example, a mixture of PMMA, chitosan, and bioglass, this powder mixture should be mixed with acrylate to form a paste and optionally an active, preferably triacrylate, for example, in the same amount and ratios as indicated for the corresponding composite and active materials described herein-above.

In embodiments of the invention, the bone cement may comprise a polymer or polymer mixture having a volume percentage of at least 20%, preferably at least 30%, preferably at least 40%, preferably at least 50%, preferably at least 60%, preferably at least 66%, and the ceramic may comprise corresponding volume percentages of at least 10%, preferably at least 15%, preferably at least 20%, preferably at least 25%, preferably at least 30%, preferably at least 33%, respectively, to make up 30%, 45%, 60%, 75%, 90% or 99%, respectively, when each of the two components (polymer/polymer mixture and ceramic/ceramic mixture) is added.

In embodiments, the bone cement can be made similarly to the implant, by addition of an amphiphilic polymer promotor. In embodiments, the amphiphilic polymer promotor is a block copolymer. In embodiments, the amphiphilic polymer promotor comprises aliphatic chains and anionic phosphate groups. In embodiments, the amphiphilic polymer promotor is an amphiphilic phosphorylated or non-phosphorylated 2-hydroxyethylmethacrylate. In embodiments, the amphiphilic polymer promoter is added by an amount of less than 30%, 20%, 10%,or 5%, preferably less than 4%, preferably less than 3%, preferably less than 2% and preferably less than 1% in weight fraction. For example, small amounts (e.g. between 0.1 and 1 weight %) of amphiphilic phosphorylated 2-hydroxyethylmethacrylate (HEMA-P) can be added providing anionic phosphate groups serving as nucleation sites for calcium phosphate phases leading to bioactivation of the bone cement surface. In embodiments, the bone cement is made with the addition of a surface property enhancer. In embodiments, the surface property enhancer is polyacrylic acid. In embodiments, the bone cement is made by mixing the first and second polymer and ceramic in powder form together with a liquid, e.g. a liquid monomer, for reacting with the bone cement material. Generally, such a mixing step produces a paste. In embodiments, the liquid serves to make an acrylate solution. The liquid may be a triacrylate, which has been found to offer improved bone growth stimulation. Triacrylates may be used alone or in a combination with other triacrylates, for example, one or more of tri-methylammonium chloride, 2-(diethylamino) ethyl 25 acrylate, PETA, TMPTMP, or combined as in PETA-co-TMPTMP, or any mixture thereof. The liquid may be a thiolacrylate, resulting in a bone implant having stimulating effect on bone cells. For example, PMMA, Bioglass® and Chitosan can be mixed in powder form with liquid methylmethacrylate monomer, or one or more of PETA, PETA-co-TMPTMP, and TMPTMP. Thus, each component of the triacrylate liquid may be used as a single acrylate, or may be mixed with another triacrylate.

According to an embodiment of the present invention, the composite polymer mixture may optionally comprise one or more filler, one or more active, and one or more amphiphilic polymer promotor.

In embodiments of the present invention, the composite polymer mixture may comprise an active such as triacrylate or acrylic acid, for example PMMA, PEEK, Bioglass (e.g. 45S5) and triacrylate. This has the advantage that bone formation may be promoted, for example by stimulation of bone cells and better adhesion of cells. For example, one or more polymer in form of a powder may be mixed with liquid triacrylate, e.g. in the following volumetric ratios of composite powder(s) to liquid triacrylate or acrylic acid (P:L): 0.25:1, 0.5:1, 0.75:1, 1:1, 1.25:1, 1.5:1, 1.75:1, 2:1 (v/v). The composite mixture may be, for example, PMMA, PEEK, Bioglass (e.g. 45S5) in a 1:1:1 ratio (v/v), PMMA, chitosan, Bioglass (e.g. 45S5) in a 1:1:1 ratio (v/v), or composite mixtures in the alternative ratios as described herein above, optionally with alternative materials as described herein above.

In an embodiment, other acrylate liquids are added such as an acrylate copolymer. For example, tri-methylammonium chloride and 2-(diethylamino) ethyl acrylate can be used. A photo-initiator can be included for UV light curing.

In embodiments of the present invention, the composite polymer mixture may comprise an amphiphilic polymer promotor which is a block copolymer. The amphiphilic polymer promotor may comprise aliphatic chains, anionic phosphate groups, or both. Illustrative examples of a suitable amphiphilic polymer promotor include amphiphilic phosphorylated 2-hydroxyethylmethacrylate and amphiphilic non-phosphorylated 2-hydroxyethylmethacrylate.

In embodiments, the implant composite material may be made with the addition of an amphiphilic polymer promotor. In embodiments, the amphiphilic polymer promotor may be a block copolymer. In embodiments, the amphiphilic polymer promotor may comprise aliphatic chains and anionic phosphate groups. In embodiments, the amphiphilic polymer promotor may be amphiphilic phosphorylated or non-phosphorylated 2-hydroxyethylmethacrylate. In embodiments, the amphiphilic polymer promoter may be added by an amount of less than 30%, 20%, 10%, or 5%, preferably less than 4%, preferably less than 3%, preferably less than 2% and preferably less than 1% in weight fraction. For example, small amounts (e.g. between 0.1 and 1 weight %) of amphiphilic phosphorylated 2-hydroxyethylmethacrylate (HEMA-P) may be added providing anionic phosphate groups serving as nucleation sites for calcium phosphate phases leading to bioactivation of the polymer surface, for example the PMMA surface.

In an embodiment, there is provided a method of making an implant, comprising mixing one or more polymer and a ceramic to provide a composite material. For example, PMMA, PEEK, and a Bioglass may be mixed to provide the composite. In embodiments, the mixing step comprises mixing PMMA, PEEK, and the ceramic in powder form with a liquid, e.g. a liquid monomer, for reacting with the PMMA material. Generally, such a mixing step produces a paste. In embodiments, the liquid serves to make an acrylate monomer solution. The liquid may be a triacrylate, which may be selected from one or more of tri-methylammonium chloride, tri-methylammonium chloride added to 2-(diethylamino) ethyl acrylate, PETA, TMPTMP, or combinations thereof, or may be used in combined form such as in PETA-co-TMPTMP. Use of triacrylate has been found to provide improved bone growth stimulation. The liquid may be a thiolacrylate, resulting in a bone implant having stimulating effect on bone cells. For example, PMMA, PEEK, and Bioglass can be mixed in powder form with liquid methylmethacrylate monomer or with PETA-co-TMPTMP or with tri-5 methylammonium chloride and 2-(diethylamino) ethyl acrylate (which has been found to stimulate bone cells).

An exemplary method of manufacture of the composite implant material comprises providing a first polymer component (e.g. PMMA powder) that will form a matrix, providing a second polymer component (e.g. PEEK powder) and a third component of ceramic (e.g. Bioglass). The three components are, in one embodiment, mixed in equal volumes of powder and mixed to form the composite. However, non-equal proportions of the three components of powders are possible, as has been described above. In addition, small amounts (0.5 wt %) of amphiphilic phosphorylated 2-hydroxyethylmethacrylate (HEMA-P) are added providing anionic phosphate groups. The PMMA and PEEK components can replicate the organic phase of natural bone, the Bioglass, as an inorganic component, can increase bioactivity of the composite and replicate the mineral component of natural bone. The promotors can serve as bioactivation of the PMMA surface. The three powder components can be mixed with liquids such as of methylmetacrylate acid (MMA), or mixed with hydroxyethyl methacrylate, or mixed with polyacrylic acid, or a combination thereof in order to produce the composite material or other liquids as described below. The liquids are added in proportions appropriate to manufacturing requirements, and mechanical and functional requirements of resulting artificial bone material. The artificial bone composite may be cured through self-curing and/or assisted by ultraviolet light or photocuring, such as ultraviolet light curing. A photo-initiator may be added to the mixture to assist the photocuring.

In an embodiment, the three powder components are mixed with a solution of PETA, or a solution of TMPTMP, or may be combined with PETA-co-TMPTMP, to make a paste. A photo-initiator can be added to the acrylate solution for a possible UV Light curing. PETA-co-TMPTMP consists of a solution containing Pentaerythriol triacrylate (PETA) with Diethylamine (DEA) and Trimethylopropane tris (3-mercaptopropionate (TMPTMP). The mixture can be prepared with any proportion for PETA with DEA the later concentration mainly ranging from 2.8-35.1% and particularly 16.1%; these two molecules are mixed with an equivalent ratio of TMPTMP, but other proportions also can be used. In another embodiment, other acrylate liquids are added such as an acrylate copolymer. For example, trimethylammonium chloride and 2-(diethylamino) ethyl acrylate can be used. A photo-initiator can be included for UV light curing. Such pastes are used in situ (e.g. implanted adjacent natural bone) or molded, printed or otherwise manufactured to make an implant outside of the body for subsequent implantation to the body.

In embodiments, the use of triacrylate, beside the advantage of promoting bone formation, has the further advantage of being a good crosslinking agent due its trifunctionality, i.e. a triacrylate monomer when reacted with PMMA can crosslink the other components of the composite, in particular, PEEK and Bioglass.

According to an embodiment of the present invention, the surface of the implant may be configured with a rough texture, including a texture that provides micro roughness or nano roughness. A rough surface may be achieved mechanically, physically, chemically, or by use of coatings. Mechanical methods include sandblasting, physical preparation include anodic oxyadation and chemical methods include surface treatments with chemicals such as acid etching. A rough surface, such as a micro or nanostructured surface, may have the advantage to improve bone to implant contact (BIC) and improve biological/secondary stability (i.e. during and after healing and bone ingrowth).

According to an embodiment of the present invention, a method of manufacture of the implant may comprise the steps of forming a 3D model of the implant site, and creating a three-dimensional implant configured to fit the 3D model. The 3D topography and abutments may be formed by a method selected from additive manufacturing, subtractive manufacturing, 3D printing, rapid prototyping, SLA additive manufacturing, Polyjet additive manufacturing, SLS additive manufacturing, and milling a block of solid implant material. Any suitable biocompatible material may be used and paired with a suitable method of manufacture based on the material properties (e.g. solid materials may be subjected to subtractive manufacturing or milling, many polymers and metals are suitable for additive manufacturing, as will be apparent to a person of ordinary skill in the art.

According to an embodiment of the present invention, the 3D model may be a virtual model created by CADCAM technology and/or 3D imaging. 3D imaging may be performed, for example, by computerized tomography (CT), Cone Beam Computerized Tomography (CBCT), magnetic resonance imaging (MRI), laser scanning, and structured light scanning.

In exemplary applications of replacement and/or bone reconstruction, the composite material is fabricated by rapid prototyping technology based on three-dimensional printing preceded by virtual planning and virtual reconstruction for the fabrication of a custom made bone implant. The presence of PMMA in the composite permits the use of printing technology based on UV curing, in the absence of PMMA. PEEK should be prepared by Fused Deposition Modelling (FDM) technology.

Figure 5:
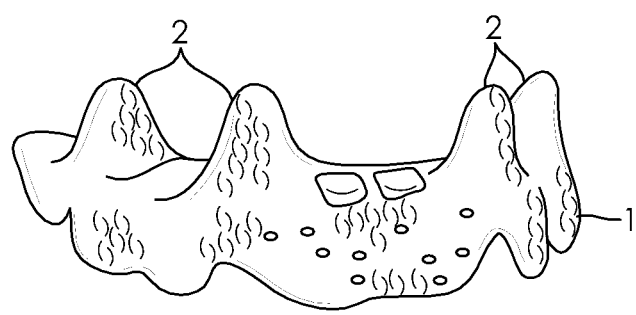
FIG. 5 shows a perspective view of an extraosseous supracrestal implant in accordance with an embodiment of the present invention.

According to an embodiment of the present invention, the additive manufacturing or 3D printing is used to manufacture the implant, and may be used to add a macroscopic structure and sub-surface metastructure, with pores or holes, see for example FIG. 5 as an illustrative example. Alternatively or in addition to the described roughly textured micro or nano surface herein, the porous metastructure has the advantage of fine-tuning and improving the mechanical, physiochemical and biological properties of the implant using various materials. In particular, by choosing a particular material and adjusting its porosity and modulus elasticity to one similar to the elastic modulus of bone structure as described herein, the stability and durability of the implant may be improved, bone ingrowth may be promoted, and deterioration may be avoided.

According to an embodiment of the present invention, the manufacture of the implant may use CAD CAM technology. For example, the process may start by 3D imaging via CT or CBCT, creating an electronic data file, for example, an STL file that may be transferred by a DICOM file, together with the image data. The data, e.g. the DICOM data, is then processed by suitable software known in the art, for example, MIMICS, Biobuild, 3D Doctor, or similar, that allow to create a 3D model of the anatomy/3D topography of interest. A computer file with a 3D model is then imported into a suitable design software, for example a haptic based environment such as Freeform® Geomagic, or a CAD based design software such as 3 Matic™ to create the final implant design and related computer file with manufacturing instructions, e.g. for machining a block of material (subtractive manufacturing) or by adding material layer by layer and fusion of the layers (additive manufacturing). Alternatively, the implant can be manually manufactured, e.g. by a lab technician, using a virtual or physical 3D model of the jaw, in particular if a polymer is used. For titanium materials, for example, EBM or SLS technology may be used for manufacture of the implant. For polymer and polymer composite materials, for example, SLA technology may be used for manufacture of the implant. These and other technologies are publicly available and can be combined depending on the chosen materials, as will be apparent to a person of ordinary skill in the art.

According to an embodiment of the present invention, as an illustrative example, the manufacture of the implant may start with 3D imaging of the bone by CBCT, then a virtual 3D model may be created with Mimic®software, then 3Matic may be used to design a corresponding virtual implant, then the virtual implant may be manufactured, or "3D printed", via a 3D printer.

In embodiments, reverse engineering and medical image-based modelling technologies may be used to construct a three-dimensional model of an anatomical structure of the human body requiring treatment or replacement. Based on the three-dimensional, a mold-less manufacturing technique may be used to build a three dimensional physical model for surgical training, preoperative planning, a customized implant or a customized scaffold for implant to a patient. The mold-less manufacturing technique may be solid free-from fabrication (SFF) or rapid prototyping (RP).

In embodiments, there is provided use of the implant described herein in a bone repair or bone reconstruction and replacement treatment.

According to an embodiment of the present invention, the prosthetic work may be done immediately or after several weeks, depending on the primary stability of the implant. For example if either bone cement or lateral, e.g. buccal or lingual, screws are used, the prosthetic work may be done immediately.

The present invention also relates to certain unique improved composite implant materials, which may be used to for the implants/supracrestal implants described hereinabove, or other dental or surgical implants (for example, endosseous implants, fixation plates, articular prosthesis, or the like).

According to an embodiment, a composite implant material may be comprising: a bone cement matrix, such as PMMA, a non-resorbable polymer, such as PEEK, and a bioactive glass filler.

The combination of PMMA, PEEK and bioactive glass filler in the implant material composite has been found to be able to be osseointegrated with natural bone in several crucial respects. Specifically, PEEK, and to a lesser extent, PMMA offer good biocompatibility, but alone still exhibit lack of bioactivity and osseointegration potential. Further, the implant material composite can be accurately shaped by a variety of manufacturing methods (examples are described below), especially custom made fabrication, even to fit complex three dimensional anatomic defects, thereby enhancing bone to implant interface and bone integration. Improved fit of a bone implant allows reduced implantation time. Yet further, the implant composite material of the present disclosure can have physical and mechanical properties (such as hardness and young modulus) that are comparable to natural bone tissue and therefore avoid mechanical mismatch between bone and implant. As a consequence osseointegration will be maintained and less bone resorption would occur at the bone-implant interface. The combination of elements of the composite can provide surface and microstructure that allows intimate integration with host bone by facilitating cell and bone in-growth and reorganization and preventing fibrous tissue interface and improve its biological activity and biocompatibility.

Without wishing to be bound by theory, it is believed that the PEEK is biocompatible polymer and can integrate with bone.

Without wishing to be bound by theory, the bioactive glass filler can form a strong bond with bone, is highly bioactive and is both osteoinductive and osteoconductive. Moreover, ionic dissolution products of the bioactive glass may enhance new bone formation (osteogenesis) through a direct control over genes that regulate cell induction and proliferation. The bioactive glass can bond with bone rapidly and its degradation (or bio resorption) can be attributed to solution—mediated dissolution stimulating bone growth away from the bone—implant interface. A mechanism for bone bonding may be through a hydroxycarbonate apatite (HCA) layer formed on the surface of the glass, following initial glass dissolution. In addition, the PMMA can have a similar density to natural bone and superior resistance to compression.

Further, without wishing to be bound by theory, PMMA when it reacts with and is crosslinked by triacrylate, it also is crosslinked to the other components, thus triacrylate serves as a crosslinking agent that integrates other components of the composite besides PMMA.

Further, and still without wishing to be bound by theory, PMMA facilitates the preparation of the composite material either by polymerisation through mixing with monomer or by using additive manufacturing using UV light curing (Stereolithography (SLA) technology). PMMA can act as a matrix for PEEK and Bioglass and as scaffold for load bearing, thereby mitigating brittle and less flexible properties of bioactive glasses. The hybridization of bioactive glasses and polymers including PMMA and PEEK can provide improved mechanical properties as well as bioactivity in the implant composite material. Accordingly, the mentioned composite disclosed herein allows enhanced healing in that structural support akin to natural bone is provided, whilst the polymers and bioactive glass phases promote tissue ingrowth such that the overall healing process following any reconstructive surgical treatment can be reduced.

In embodiments, the implant composite material of the present disclosure falls within a traditional definition of a composite material. Namely, a material with at least two phases (three phases here), a continuous phase, PMMA, and PEEK and a dispersed phase, bioactive glass. The continuous phase can fill the volume and transfer loads to the dispersed phase. The dispersed phase can enhance one or more properties of the composite such as biocompatibility and ingrowth promotion.

In embodiments, the bioactive glass filler includes silicon dioxide and calcium oxide as major constituents. For example, the bioactive glass filler may comprise at least 25% by weight of each of silicon dioxide and calcium oxide. In embodiments, the bioactive glass filler is composition 45S5 or Bioglass. The bioactive glass filler may have the composition 46.1 mol. % $SiO_2$, 24.4 mol. % $Na_2O$, 26.9 mol. % $CaO$—$SiO_2$ and 2.6 mol % $P_2O_5$.

In embodiments, the bioactive glass is biodegradable.

In embodiments, the PEEK and PMMA are non resorbable polymers and are particularly apt to replicate various mechanical characteristics of natural bone.

In embodiments, PMMA, PEEK and the bioactive glass filler each have a volume fraction of at least 10%, preferably at least 15%, preferably at least 20%, preferably at least 25%, preferably at least 30%, preferably at least 33%. In embodiments, PMMA, PEEK and the bioactive glass filler substantially equivalent volumetric fractions. However, the volumetric fractions can be varied as desired depending upon the application, specifically depending upon mechanical and biological properties required by the application. For example, should reduced stiffness be required, then a fractional reduction in bioactive glass and fractional increase in polymer from equal volumes can be implemented.

In embodiments, the implant composite material can be made with the addition of an amphiphilic polymer promotor. In embodiments, the amphiphilic polymer promotor is a block copolymer. In embodiments, the amphiphilic polymer promotor comprises aliphatic chains and anionic phosphate groups. In embodiments, the amphiphilic polymer promotor is amphiphilic phosphorylated or non-phosphorylated 2-hydroxyethylmethacrylate. In embodiments, the amphiphilic polymer promotor is added by an amount of less than 30%, 20%, 10%,or 5%, preferably less than 4%, preferably less than 3%, preferably less than 2% and preferably less than 1% in weight fraction.

For example, small amounts (e.g. between 0.1 and 1 weight %) of amphiphilic phosphorylated 2-hydroxyethylmethacrylate (HEMA-P) can be added providing anionic phosphate groups serving as nucleation sites for calcium phosphate phases leading to bioactivation of the PMMA surface.

In embodiments, the composite implant material might be useful in fabricating implant for bone defect reconstruction by using osseointegrated implant that can support any functional or aesthetic prosthesis. In embodiments, the composite implant material is useful in orthopedic surgery and craniofacial reconstructive or plastic surgery. In embodiments, the bone implant composite is useful in oral surgery to fabricate commercialize dental implant, jaw implant as well as custom made dental implant, jaw implant and prosthetic component and accessories.

In embodiments, the bone implant is to augment or replace a load bearing bone or a non-load bearing bone.

In embodiments, the bone implant is a craniofacial or a maxillofacial bone implant, such as a jaw bone implant. The bone implant can be useful in hip replacement and other replacement applications as well as repair applications.

The bone implant can be a customized bone implant, which may be made according to the methods suitable for producing customized, patient specific, bone implants.

The bone implant composite can be provided in the form of, a block for processing to produce a bone implant, as paste, as feeding material for a three dimensional printer or as a shaped bone implant.

In embodiments, the use comprises making the bone implant using rapid prototyping, additive manufacturing or subtractive manufacturing. Rapid prototyping and additive manufacturing may encompass making the bone implant using three-dimensional printing to reconstruct an electronic three-dimensional model of the bone implant. The electronic three-dimensional model can be constructed based on imaging of a target site of a patient. The imaging can be X-ray imaging such as CT scanning or magnetic resonance imaging (MRI) or a combination thereof. Subtractive manufacturing can include producing a block of the composite implant material and forming the implant by subtractive processing such as milling.

In embodiments, the use of one or more triacrylate as the liquid has been found to provide a unique composite material that compared to a composite made using monomeric MMA liquid provides various benefits, including improved bone growth stimulation when used as bone implant, due to having a stimulating effect on bone cells.

Surprisingly, a composite material formed from PEEK, Bioglass and PMMA powder when mixed with liquid triacrylate as a monomer has unique characteristics that allow its use in surgical and dental applications, and include an advantageous stimulatory effect on bone growth and other improved characteristics compared to previously available materials. Without wishing to be bound by theory, it is believed that the trifunctional monomer crosslinks PMMA and uniquely integrates the other components (PEEK and bioglass), resulting in a material with various desirable characteristics as described herein which is ideally suited for surgical and dental applications (e.g. the composite may be formed so that it mimics the porosity and modulus of natural bone more closely), in addition to providing a bone growth stimulatory effect.

In an embodiment, the powder mixture may consist of three components in powder form selected from the group consisting of PEEK, PMMA and Bioglass, and the percentage (v/v) of PMMA to the remaining powder components (i.e. PEEK, Bioglass) may be from about 5% to about 33%.

In a preferred embodiment, the composite is prepared by mixing the powder mixture with a triacrylate liquid selected from the group consisting of trimethylammonium chloride, pentaerythritol triacrylate, trimethylolpropane, and combinations thereof.

In an embodiment, the powder components may be mixed with liquid triacrylate in an amount sufficient to form a paste. For example, one or more polymer in form of a powder may be mixed with liquid triacrylate or acrylic acid, e.g. in the following volumetric ratios of composite powder(s) to liquid triacrylate or acrylic acid (P:L): 0.25:1, 0.5:1, 0.75:1, 1:1, 1.25:1, 1.5:1, 1.75:1, 2:1 (v/v).

For example, the triacrylate liquid may comprise trimethylammonium chloride, pentaerythritol triacrylate, and trimethylolpropane, for example in about equal amounts. Alternatively, the triacrylate liquid may comprise trimethylammonium chloride and pentaerythritol triacrylate, in about equal amounts. Still alternatively, the triacrylate liquid may comprise pentaerythritol triacrylate and trimethylolpropane in about equal amounts. Also, the triacrylate liquid may comprise trimethylammonium chloride and trimethylolpropane in about equal amounts.

In an embodiment, a photo-initiator can be included in the composite mixture for UV light curing. The resulting paste may be used in situ (e.g. implanted adjacent to natural bone) or molded, printed or otherwise manufactured to make an implant outside of the body for subsequent implantation to the body.

In an embodiment, the proportion of liquid triacrylate to powders (PEEK, bioglass, PMMA) may vary depending on the desired surgical/dental application, and may also depend on the fabrication process.

In an embodiment, for example, for conventional curing, a useful ratio may be about 30 to about 50%, for example about 40% triacrylic liquid (with the corresponding remainder formed by the powders, e.g. from about 50% to about 70%, for example about 60% of powders). The resulting paste will be hardened and cured, e.g. by UV.

In an embodiment, for 3D printing, a lower viscosity mixture suitable for processing in a 3D printer may be used. For example, the percentages of liquid to powders may be from about 60% to about 80% or more of liquid triacrylate (with the corresponding 40% to about 20% or less formed by the powders, and any optional additives).

In embodiments, a preferred optional additive is a small amount (e.g. between 0.1 and 1 weight %) of amphiphilic phosphorylated 2-hydroxyethylmethacrylate (HEMA-P) which can be added to providing anionic phosphate groups serving as nucleation sites for calcium phosphate phases leading to bioactivation of the PMMA surface. HEMA-P or other additives in amounts as described hereinabove may be added.

In another aspect of the present disclosure, there is provided a method of making a bone implant, comprising mixing PMMA, PEEK, and a bioactive glass filler to provide a bone implant composite.

In embodiments, the method comprises obtaining three-dimensional imaging of a treatment site, determining a three dimensional model of the treatment site based on the three-dimensional imaging and making the bone implant based on the model. The three-dimensional imaging may comprise computerized tomography (CT), magnetic resonance imaging (MRI), and laser (or structured light) scanning.

In embodiments, CADCAM technology is used in making the bone implant.

In embodiments, the step of making the bone implant comprises three-dimensional printing with the composite implant material as feeding material therefor.

In embodiments, the method comprises making a customized bone block or customized implant, such as through three-dimensional printing or molding.

In embodiments, the method comprises curing the bone implant composite. In embodiments, the curing is through, or assisted through, electromagnetic waves such as ultraviolet light. In other embodiments curing takes place through self-curing and/or is assisted by photocuring.

In embodiments, the mixing includes adding a photo-initiator and curing through, or assisting curing through, the bone implant composite using application of light. In embodiments, the bone composite is made into a paste and subsequently photocured or cured with assistance of light such as ultraviolet light. For example, self-curing with light assistance is envisaged.

In embodiments, the preparation can be done by three-dimensional printing (additive manufacturing).

In embodiments, the mixing step comprises mixing PMMA, PEEK, and bioactive glass filler material in powder form with a liquid, e.g. a liquid monomer, for reacting with the PMMA material. Generally, such a mixing step produces a paste. In embodiments, the liquid serves to make an acrylate solution. The liquid may be a triacrylate such as tri-methylammonium chloride and 2-(diethylamino) ethyl acrylate or PETA-co-TMPTMP. Use of triacrylate has been found to provide improved bone growth stimulation. The liquid may be a thiolacrylate, resulting in a bone implant having stimulating effect on bone cells. For example, PMMA, PEEK, and Bioglass can be mixed in powder form with liquid methylmethacrylate monomer or with PETA-co-TMPTMP or with tri-methylammonium chloride (which has been found to stimulate bone cells).

In embodiments, the making step comprises milling a block of the composite implant material.

In embodiments, reverse engineering and medical image-based modelling technologies are used to construct a three-dimensional model of an anatomical structure of the human body requiring treatment or replacement. Based on the three-dimensional, a mold-less manufacturing technique can be used to build a three dimensional physical model for surgical training, preoperative planning, a customized implant or a customized scaffold for implant to a patient. The mold-less manufacturing technique may be solid free-from fabrication (SFF) or rapid prototyping (RP).

In yet another aspect, there is provided use of the composite implant material of described herein in a bone repair or bone reconstruction and replacement treatment. The treatment can be any of the medical treatments disclosed herein.

The various features disclosed above with respect to the bone implant composite are applicable to the use and method aspects described herein.

These and other aspects of the invention will be apparent from and elucidated with reference to the embodiment(s) described hereinafter.

DETAILED DESCRIPTION OF AN EXEMPLARY EMBODIMENT

An exemplary method of manufacture of the composite implant material comprises providing a first component of PMMA powder that will form a matrix, providing a second component of PEEK powder and a third component of Bioglass powder as a filler. The three components are, in one embodiment, mixed in equal volumes of powder and mixed to form the composite. However, non-equal proportions of the three components of powders are possible, as has been described above. In addition, small amounts (0.5 wt %) of amphiphilic phosphorylated 2-hydroxyethylmethacrylate (HEMA-P) are added providing anionic phosphate groups. The PMMA and PEEK components can replicate the organic phase of natural bone, the Bioglass, as an inorganic component, can increase bioactivity of the composite and replicate the mineral component of natural bone. The promotors can serve as bioactivation of the PMMA surface.

The three powder components can be mixed with one or more liquid such as triacrylate, hydroxyethylmethacrylate, polyacrylic acid, or a combination thereof, or with another liquid as described below, in order to produce the composite material. The liquids are added in proportions appropriate to manufacturing requirements, and mechanical and functional requirements of the resulting artificial bone material.

The implant composite material may be cured through self-curing and/or assisted by ultraviolet light or photocuring, such as ultraviolet light curing. A photo-initiator may be added to the mixture to assist the photocuring or light curing. A photo-initiator may be added to the mixture to assist the photocuring.

In another embodiment, chitosan may be used instead of PEEK in the artificial bone composite for the same purpose, and may be cured through self-curing and/or assisted by ultraviolet light or photocuring, such as ultraviolet light curing. A photo-initiator may be added to the mixture to assist the photocuring or light curing.

In another embodiment, the three powder components are mixed with a solution of PETA-co-TMPTMP to make a paste, or a viscous solution. A photo-initiator can be added to the acrylate solution for a possible UV Light curing. PETA-co-TMPTMP consists of a solution containing Pentaerythriol triacrylate (PETA) with Diethylamine (DEA) and Trimethylopropane tris(3-mercaptopropionate (TMPTMP). The mixture can be prepared in any proportion of PETA to DEA, however, without limitation, a DEA concentration ranging from about 2.8% to about 35.1%, and particularly of about 16.1%, may be preferred. A mixture of PETA and DEA may be mixed with an equal ratio of TMPTMP (PETA/DEA:TMPTMP of about 1:1), but other proportions also can be used.

In yet another embodiment, other acrylate liquids are added, such as an acrylate copolymer. For example, trimethylammonium chloride and 2-(diethylamino) ethyl acrylate can be used. A photo-initiator can be included for UV light curing.

Such pastes are used in situ (e.g. implanted adjacent natural bone) or molded, printed or otherwise manufactured to make an implant outside of the body for subsequent implantation to the body.

Similarly, in embodiments, one or more triacrylate monomer may be used in combination with one or more copolymer in a mixture. These mixtures (e.g. pastes or solutions) may include an added polymerization inhibitor, to prevent a premature polymerization and curing of the paste or the solution, i.e. a curing before the composite mixture can be shaped either by 3D Printing of the solution or by shaping the paste into a particular form. The inhibitor prevents premature curing and allows to control it by other means, in particular by UV light.

The composite material manufactured as just described can be used to reconstruct and replace any bone defect in the body including in cranio, maxillofacial, and orthopedic applications, and any osseointegrated implant that can support a functional or aesthetic prosthesis, specifically for jaw defects in implant dentistry practice, e.g. to replace a tooth with a dental implant or endosseous implant.

The bone implants described herein can be fixed to the patient in any way such as through use of at least one mechanical fastener (for example, a screw) or used as an endosseous implant.

In exemplary applications of replacement and/or bone reconstruction, the composite material is fabricated by rapid prototyping technology based on three-dimensional printing preceded by virtual planning and virtual reconstruction for the fabrication of a custom made bone implant. The presence of PMMA in the composite permits the use of printing technology based on UV curing, in the absence of PMMA. PEEK should be prepared by Fused Deposition Modelling (FDM) technology.

DETAILED DESCRIPTION OF THE DRAWINGS

Exemplary Embodiments

Figure 2:
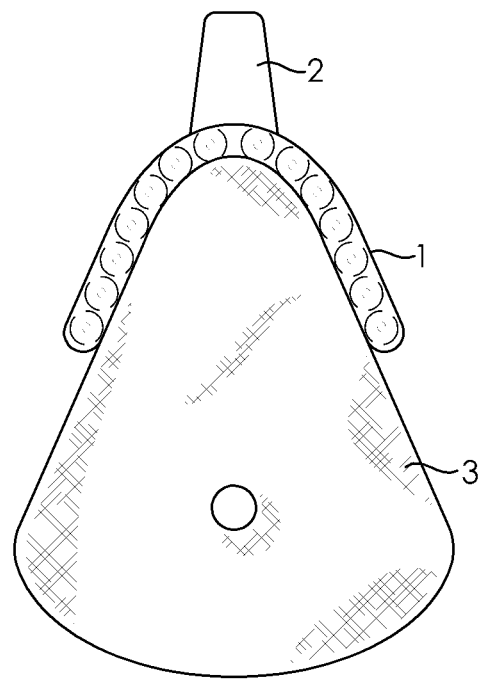
FIG. 2 shows a schematic sectional view of an extraosseous supracrestal implant in accordance with an embodiment of the present invention.
Figure 3:
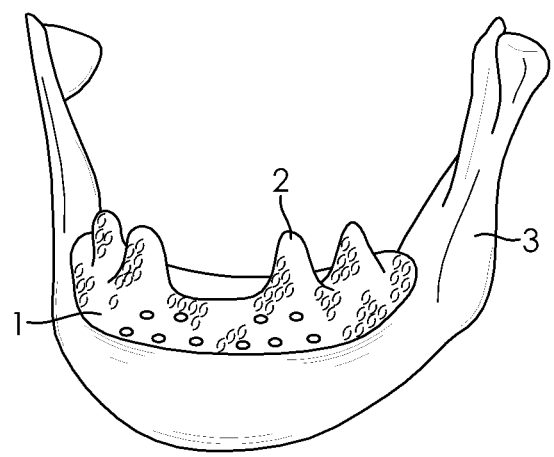
FIG. 3 shows a perspective view of an extraosseous supracrestal implant in accordance with an embodiment of the present invention.
Figure 4:
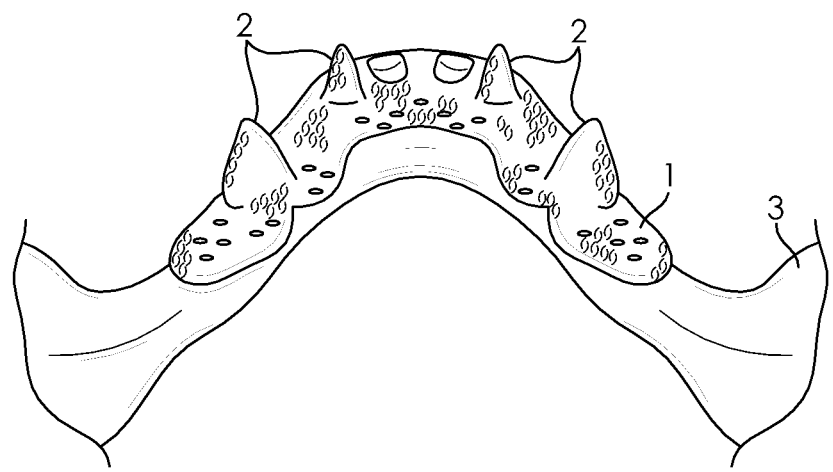
FIG. 4 shows a perspective view of an extraosseous supracrestal implant in accordance with an embodiment of the present invention.

Turning to FIG. 1, a schematic view of an extraosseous implant (1) in accordance with an embodiment of the present invention is shown, in particular a supra crestal implant onto a lower jaw bone (3); this particular implant has four abutments (2);

Turning to FIG. 2, a schematic sectional view of an extraosseous supra crestal implant (1) in accordance with an embodiment of the present invention is shown, in particular a cross section through a supra crestal implant onto a lower jaw bone (3);

Turning to FIG. 3, a perspective view of an extraosseous supra crestal implant (1) in accordance with an embodiment of the present invention is shown, in particular a front view of a supra crestal implant onto a lower jaw bone (3), showing the buccal surface;

Turning to FIG. 4, a perspective view of an extraosseous supra crestal implant (1) in accordance with an embodiment of the present invention is shown, in particular a back view of a supra crestal implant onto a lower jaw bone (3), showing the lingual surface;

Turning to FIG. 5, a perspective view of an extraosseous supra crestal implant in accordance with an embodiment of the present invention is shown, in particular a front view of a supra crestal implant (1), showing its macroscopic porosity.

Figure 6:
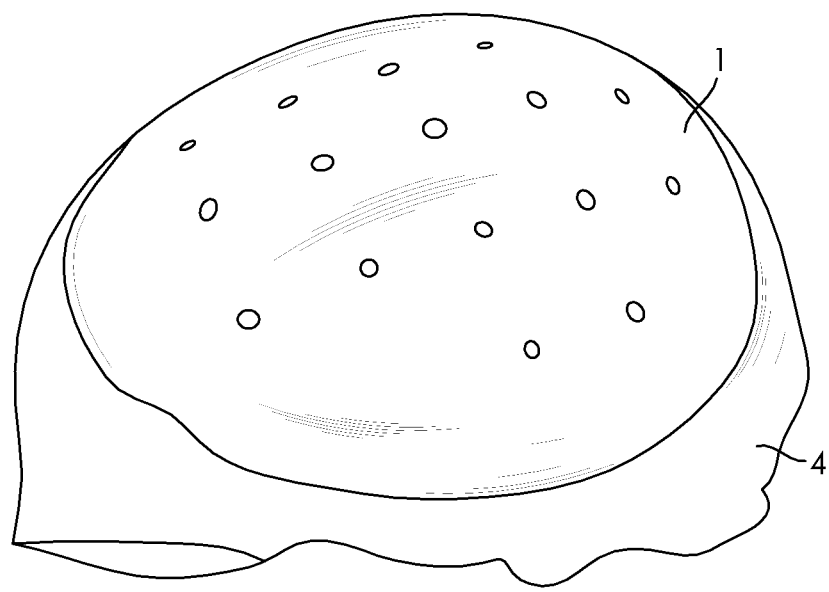
FIG. 6 shows a schematic view of skull implant (cap) made using the composite implant material disclosed herein.

FIG. 6 is a schematic view of an exemplary implant (1) made using the composite implant material disclosed herein; it shows one exemplary implant application of the composite implant material disclosed herein. Specifically, a skull implant has been made, which is a skull cap in the figure, sitting on the skull bone (4).

Figure 7:
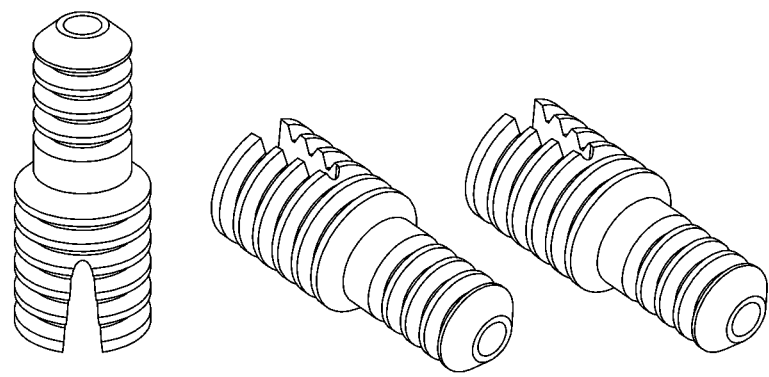
FIG. 7 is a schematic view of a dental implant made using the composite implant material disclosed herein.

FIG. 7 is a schematic view of another exemplary implant (1) made using the composite implant material disclosed herein; shows another exemplary implant application of the composite implant material disclosed herein. Specifically, a dental implant has been made.

It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments.

While multiple embodiments are disclosed, still other embodiments of the present invention will become apparent to those skilled in the art from this detailed description. The invention is capable of myriad modifications in various obvious aspects, all without departing from the spirit and scope of the present invention. Accordingly, the drawings and descriptions are to be regarded as illustrative in nature rather than restrictive.

The invention claimed is:

1. A composite composition comprising PEEK, bioglass and PMMA, wherein the composite is formed by mixing PEEK, bioglass and PMMA with a triacrylate liquid.

2. The composition of claim 1 further comprising HEMA-P.

3. A method of 3D printing a dental implant, wherein PEEK, bioglass and PMMA powders are mixed with a triacrylate liquid, and the resulting liquid mixture is used to form the implant in a 3D printing process.

* * * * *